United States Patent
Imoto et al.

(10) Patent No.: US 7,691,594 B2
(45) Date of Patent: Apr. 6, 2010

(54) ANTICANCER AGENT

(75) Inventors: Issei Imoto, Tokyo (JP); Johji Inazawa, Tokyo (JP); Hiroyuki Izumi, Tokyo (JP); Sana Yokoi, Tokyo (JP)

(73) Assignees: Fujifilm Corporation, Tokyo (JP); Tokyo Medical and Dental University, Tokyo (JP)

(*) Notice: Subject to any disclaimer, the term of this patent is extended or adjusted under 35 U.S.C. 154(b) by 256 days.

(21) Appl. No.: 11/723,694

(22) Filed: Mar. 21, 2007

(65) Prior Publication Data

US 2008/0299184 A1 Dec. 4, 2008

(30) Foreign Application Priority Data

Mar. 22, 2006 (JP) .............................. 2006-078786

(51) Int. Cl.
*G01N 33/574* (2006.01)
(52) U.S. Cl. .......................................... 435/7.23; 435/6
(58) Field of Classification Search ........................ None
See application file for complete search history.

(56) References Cited

U.S. PATENT DOCUMENTS

2006/0165708 A1 7/2006 Mayumi et al.
2008/0095764 A1* 4/2008 Parsons et al. ........... 424/130.1

FOREIGN PATENT DOCUMENTS

| EP | 1 225 222 A1 | | 7/2002 |
| WO | WO-02/072771 A2 | | 9/2002 |
| WO | WO 2004/048938 | * | 6/2004 |
| WO | WO-2006/009915 A2 | | 1/2006 |

OTHER PUBLICATIONS

Imoto et al., Cancer Research, vol. 66, No. 9, pp. 4617-4626, May 1, 2006.
Ying et al., Oncogene, vol. 25, No. 7, pp. 1070-1080, Feb. 16, 2006.
Database UniProt (online) Protocadherein—20, Aug. 16, 2004, XP-002435136.
Yagi et al., Genes & Development, vol. 14, No. 10, pp. 1169-1180, May 15, 2000.
Yamashita et al., World J Gastroenterol, vol. 11, No. 33, 2005, pp. 5129-5135.

* cited by examiner

*Primary Examiner*—Misook Yu
*Assistant Examiner*—Mark Halvorson
(74) *Attorney, Agent, or Firm*—Birch, Stewart, Kolasch & Birch, LLP

(57) ABSTRACT

It is an object of the present invention to provide a cancer-suppressing agent comprising a novel cancer-suppressing gene based on the discovery of such cancer-suppressing gene. The present invention provides A cancer-suppressing agent which comprises PCDH20 gene or a homologous gene thereof.

1 Claim, 4 Drawing Sheets

A

B

C

SEQUENCE LISTING

<160> NUMBER OF SEQ ID NOS: 2

<210> SEQ ID NO 1
<211> LENGTH: 4412
<212> TYPE: DNA
<213> ORGANISM: Homo sapiens

<400> SEQUENCE: 1

```
gagggaatgc gcgcagctca caggccctgg gagtgagctg gtgcccggcg acctggcacc        60
cgcgcctgga tatgggcgt  ctacatcgtc ccaggagcag caccagctac aggaacctgc       120
cgcatctgtt tctgtttttc ctcttcgtgg gaccct tcag ctgcctcggg agttacagcc       180
gggccaccga gcttctgtac agcctaaacg agggactacc cgcggggggtg ctcatcggca      240 gcctggccga ggacctgcgg ctgctgccca ggtctgcagg gaggccggac ccgcagtcgc       300
```

```
agctgccaga gcgcaccggt gctgagtgga accccctct ctccttcagc ctggcctccc    360
ggggactgag tggccagtac gtgaccctag acaaccgctc tggggagctg cacacttcag    420
ctcaggagat cgacagggag gccctgtgtg ttgaagggg tggagggact gcgtggagcg    480
gcagcgtttc catctcctcc tctccttctg actcttgtct tttgctgctg gatgtgcttg    540
tcctgcctca ggaatacttc aggtttgtga aggtgaagat cgccatcaga gacatcaatg    600
acaacgcccc gcagttccct gtttcccaga tctcggtgtg ggtcccggaa aatgcacctg    660
taaacacccg actggccata gagcatcctg ctgtggaccc agatgttggc attaatgggg    720
ttcagaccta tcgcttactg gactaccatg gtatgttcac cctggacgtg gaggagaatg    780
agaatgggga gcgcaccccc tacctaattg tcatgggtgc tttggacagg gaaacccagg    840
accagtatgt gagcatcatc acagctgagg atggtgggtc tccaccactt ttgggcagtg    900
ccactctcac cattggcatc agtgacatta atgacaattg ccctctcttc acagactcac    960
aaatcaatgt cactgtgtat gggaatgcta cagtgggcac cccaattgca gctgtccagg   1020
ctgtggataa agacttgggg accaatgctc aaattactta ttcttacagt cagaaagttc   1080
cacaagcatc taaggattta tttcacctgg atgaaaacac tggagtcatt aaactttca    1140 gtaagattgg aggaagtgtt ctggagtccc acaagctcac catccttgct aatggaccag   1200
gctgcatccc tgctgtaatc actgctcttg tgtccattat aaagttatt ttcagacccc    1260 ctgaaattgt ccctcgttac atagcaaacg agatagatgg tgttgtttat ctgaaagaac    1320
tggaacccgt taacactccc attgcgtttt tcaccataag agatccagaa ggtaaataca    1380
aggttaactg ctacctggat ggtgaagggc cgtttaggtt atcaccttac aaaccataca    1440
ataatgaata tttactagag accacaaaac ctatggacta tgagctacag cagttctatg    1500
aagtagctgt ggtggcttgg aactctgagg gatttcatgt caaaagggtc attaaagtgc    1560 aactttaga tgacaatgat aatgctccaa ttttccttca acccttaata gaactaacca    1620
tcgaagagaa caactcaccc aatgcctttt tgactaagct gtatgctaca gatgccgaca    1680
gcgaggagag aggccaagtt tcatattttc tgggacctga tgctccatca tattttcct    1740 tagacagtgt cacaggaatt ctgacagttt ctactcagct ggaccgagaa gagaaagaaa   1800
agtacagata cactgtcaga gctgttgact gtgggaagcc acccagagaa tcagtagcca   1860
ctgtggccct cacagtgttg gataaaaatg acaacagtcc tcggtttatc aacaaggact   1920
tcagcttttt tgtgcctgaa aactttccag gctatggtga gattggagta attagtgtaa   1980
cagatgctga cgctggacga aatggatggg tcgccctctc tgtggtgaac cagagtgata   2040
tttttgtcat agatacagga aagggtatgc tgagggctaa agtctctttg gacagagagc   2100
agcaaagctc ctatacttg tggggttgaag ctgttgatgg gggtgagcct gcctctcct    2160 ctacagcaaa aatcacaatt ctccttctag atatcaatga caaccctcct cttgttttgt   2220
ttcctcagtc taatatgtct tatctgttag tactgccttc tactctgcca ggctccccgg   2280
ttacagaagt ctatgctgtc gacaaagaca caggcatgaa tgctgtcata gcttacagca   2340
tcatagggag aagaggtcct aggcctgagt ccttcaggat tgaccctaaa actggcaaca   2400
ttactttgga agaggcattg ctgcagacag attatgggct ccatcgctta ctggtgaaag   2460
tgagtgatca tggttatccc gagcctctcc actccacagt catggtgaac ctatttgtca   2520
atgacactgt cagtaatgag agttacattg agagtctttt aagaaaagaa ccagagatta   2580
atatagagga gaaagaacca caaatctcaa tagaaccgac tcataggaag gtagaatctg   2640
tgtcttgtat gcccaccta gtagctctgt ctgtaataag cttggggttcc atcacactgg   2700
```

```
tcacagggat gggcatatac atctgtttaa ggaaagggga aaagcatccc agggaagatg    2760
aaaatttgga agtacagatt ccactgaaag gaaaaattga cttgcatatg cgagagagaa    2820
agccaatgga tatttctaat atttgatatt tcatggtgga ataacacaga gaaatgtttt    2880
aactgacttt ggatcttcat cacctaaaaa agagtgtgtt gatggcagtt ccaatgaagg    2940
acaactaatt tataacttgt tctatattgt aaatagctgt ttacaggttt ttaaatttaa    3000
attcagaggt tataaaatgt gtacagcatt tttaagtgaa aattagtact aacagctata    3060
ggacttgtat ttaaaaaaaa aaaaaaaaaa agcttggaca tggtttgcag ctttcataca    3120
ccaagcagtt gattgataaa acctgggagt aaggtaagaa aaatggaaca aattttatc    3180 taaaaattcc tgtcaccaca agagggcatc agctgctcct ttgcaggaaa ctggggtatt    3240
gtacttggca gttgtacatg aaattaatga aagagtatat tttaaatata ttgttttaa    3300 cattaaacaa atatgaaatt aaagtaaatt aaatttcacc ctatttaaac atatgataaa    3360
aaaagaaatg cacttgtaaa cagaatgttt attacctcat aagtgcatat atagtttgaa    3420
agagaaggca ttaaaagaa gtgcgattcc ttttttagcaa ggataaaatc attgccttgt    3480
gttacagatt cagcctgctg aagagtattc cactttctgt gtactcgaat tgctttctgt    3540
ttgctttacc actgcacttg ttattattac aagggaaata gatatataca tacatatata    3600
tattcttcat tacaggaaat gtaactagat attgtgccca agaaaacag ccagaagcaa     3660 agaaatgctt caatctttag ttgcttcata ggcattcatg acattttagt gctttcacaa    3720
cttgttggtc gtactttata cttgggttat atattagact tttataggct tgaaatcatc    3780
catcacataa gaaatagaa atcatattaa aagtgaattc ttctagaggc ttgtgtacac     3840
tactggttgt tttagttggg cctttttatat gaaagttata ctgtacttat cttttttgttg   3900 ttgtttaggt ttgttgacta ccatttctgg cttcctttct ttggttttgg attaaatcca    3960
acagtttatt tgtaagccct gcagcagatt tctttgataa tttagctttt actgaatctc    4020
ttgcaatgaa gaaagctatt tcatcagtga tttatcactt tcaattcatt gtgtgagctg    4080
gaaatattat tttatatgag agctatagca aaataatctg tataaacaag gaatgtgtta    4140
gcttaaactg gatcatttta cttttttggca tcatgcatct gtactgtacc aaaagtgttt    4200
atatgtctgc aaattaaagg tatatatttt cataatttct ttctcacttt tagcatttta    4260
tatttgaaca tgggcttgtt atttcactga agtgcctgtc atttgtttgt ttttagggtt    4320
aaatgtgggt aacctgtagt attctgctat actaaagttt atattaaatg aattcattac    4380
tcaattaaac attgggtaaa ttattaaaaa aa                                  4412
```

<210> SEQ ID NO 2
<211> LENGTH: 924
<212> TYPE: PRT
<213> ORGANISM: Homo sapiens

<400> SEQUENCE: 2

```
Met Gly Arg Leu His Arg Pro Arg Ser Ser Thr Ser Tyr Arg Asn Leu
 1               5                  10                  15

Pro His Leu Phe Leu Phe Phe Leu Phe Val Gly Pro Phe Ser Cys Leu
                20                  25                  30

Gly Ser Tyr Ser Arg Ala Thr Glu Leu Leu Tyr Ser Leu Asn Glu Gly
            35                  40                  45

Leu Pro Ala Gly Val Leu Ile Gly Ser Leu Ala Glu Asp Leu Arg Leu
        50                  55                  60
```

```
Leu Pro Arg Ser Ala Gly Arg Pro Asp Pro Gln Ser Gln Leu Pro Glu
 65                  70                  75                  80

Arg Thr Gly Ala Glu Trp Asn Pro Pro Leu Ser Phe Ser Leu Ala Ser
                 85                  90                  95

Arg Gly Leu Ser Gly Gln Tyr Val Thr Leu Asp Asn Arg Ser Gly Glu
            100                 105                 110

Leu His Thr Ser Ala Gln Glu Ile Asp Arg Glu Ala Leu Cys Val Glu
            115                 120                 125

Gly Gly Gly Gly Thr Ala Trp Ser Gly Ser Val Ser Ile Ser Ser Ser
130                 135                 140

Pro Ser Asp Ser Cys Leu Leu Leu Asp Val Leu Val Leu Pro Gln
145                 150                 155                 160

Glu Tyr Phe Arg Phe Val Lys Val Lys Ile Ala Ile Arg Asp Ile Asn
                165                 170                 175

Asp Asn Ala Pro Gln Phe Pro Val Ser Gln Ile Ser Val Trp Val Pro
            180                 185                 190

Glu Asn Ala Pro Val Asn Thr Arg Leu Ala Ile Glu His Pro Ala Val
            195                 200                 205

Asp Pro Asp Val Gly Ile Asn Gly Val Gln Thr Tyr Arg Leu Leu Asp
210                 215                 220

Tyr His Gly Met Phe Thr Leu Asp Val Glu Glu Asn Glu Asn Gly Glu
225                 230                 235                 240

Arg Thr Pro Tyr Leu Ile Val Met Gly Ala Leu Asp Arg Glu Thr Gln
                245                 250                 255

Asp Gln Tyr Val Ser Ile Ile Thr Ala Glu Asp Gly Gly Ser Pro Pro
            260                 265                 270

Leu Leu Gly Ser Ala Thr Leu Thr Ile Gly Ile Ser Asp Ile Asn Asp
            275                 280                 285

Asn Cys Pro Leu Phe Thr Asp Ser Gln Ile Asn Val Thr Val Tyr Gly
290                 295                 300

Asn Ala Thr Val Gly Thr Pro Ile Ala Ala Val Gln Ala Val Asp Lys
305                 310                 315                 320

Asp Leu Gly Thr Asn Ala Gln Ile Thr Tyr Ser Tyr Ser Gln Lys Val
                325                 330                 335

Pro Gln Ala Ser Lys Asp Leu Phe His Leu Asp Glu Asn Thr Gly Val
            340                 345                 350

Ile Lys Leu Phe Ser Lys Ile Gly Gly Ser Val Leu Glu Ser His Lys
            355                 360                 365

Leu Thr Ile Leu Ala Asn Gly Pro Gly Cys Ile Pro Ala Val Ile Thr
370                 375                 380

Ala Leu Val Ser Ile Ile Lys Val Ile Phe Arg Pro Pro Glu Ile Val
385                 390                 395                 400

Pro Arg Tyr Ile Ala Asn Glu Ile Asp Gly Val Val Tyr Leu Lys Glu
                405                 410                 415

Leu Glu Pro Val Asn Thr Pro Ile Ala Phe Phe Thr Ile Arg Asp Pro
            420                 425                 430

Glu Gly Lys Tyr Lys Val Asn Cys Tyr Leu Asp Gly Glu Gly Pro Phe
            435                 440                 445

Arg Leu Ser Pro Tyr Lys Pro Tyr Asn Glu Tyr Leu Leu Glu Thr
450                 455                 460

Thr Lys Pro Met Asp Tyr Glu Leu Gln Gln Phe Tyr Glu Val Ala Val
465                 470                 475                 480

Val Ala Trp Asn Ser Glu Gly Phe His Val Lys Arg Val Ile Lys Val
```

-continued

```
            485                 490                 495
Gln Leu Leu Asp Asp Asn Asp Asn Ala Pro Ile Phe Leu Gln Pro Leu
            500                 505                 510

Ile Glu Leu Thr Ile Glu Glu Asn Asn Ser Pro Asn Ala Phe Leu Thr
            515                 520                 525

Lys Leu Tyr Ala Thr Asp Ala Asp Ser Glu Glu Arg Gly Gln Val Ser
            530                 535                 540

Tyr Phe Leu Gly Pro Asp Ala Pro Ser Tyr Phe Ser Leu Asp Ser Val
545                 550                 555                 560

Thr Gly Ile Leu Thr Val Ser Thr Gln Leu Asp Arg Glu Glu Lys Glu
                565                 570                 575

Lys Tyr Arg Tyr Thr Val Arg Ala Val Asp Cys Gly Lys Pro Pro Arg
                580                 585                 590

Glu Ser Val Ala Thr Val Ala Leu Thr Val Leu Asp Lys Asn Asp Asn
                595                 600                 605

Ser Pro Arg Phe Ile Asn Lys Asp Phe Ser Phe Phe Val Pro Glu Asn
            610                 615                 620

Phe Pro Gly Tyr Gly Glu Ile Gly Val Ile Ser Val Thr Asp Ala Asp
625                 630                 635                 640

Ala Gly Arg Asn Gly Trp Val Ala Leu Ser Val Val Asn Gln Ser Asp
                645                 650                 655

Ile Phe Val Ile Asp Thr Gly Lys Gly Met Leu Arg Ala Lys Val Ser
                660                 665                 670

Leu Asp Arg Glu Gln Gln Ser Ser Tyr Thr Leu Trp Val Glu Ala Val
            675                 680                 685

Asp Gly Gly Glu Pro Ala Leu Ser Ser Thr Ala Lys Ile Thr Ile Leu
            690                 695                 700

Leu Leu Asp Ile Asn Asp Asn Pro Pro Leu Val Leu Phe Pro Gln Ser
705                 710                 715                 720

Asn Met Ser Tyr Leu Leu Val Leu Pro Ser Thr Leu Pro Gly Ser Pro
                725                 730                 735

Val Thr Glu Val Tyr Ala Val Asp Lys Asp Thr Gly Met Asn Ala Val
                740                 745                 750

Ile Ala Tyr Ser Ile Ile Gly Arg Arg Gly Pro Arg Pro Glu Ser Phe
                755                 760                 765

Arg Ile Asp Pro Lys Thr Gly Asn Ile Thr Leu Glu Glu Ala Leu Leu
            770                 775                 780

Gln Thr Asp Tyr Gly Leu His Arg Leu Leu Val Lys Val Ser Asp His
785                 790                 795                 800

Gly Tyr Pro Glu Pro Leu His Ser Thr Val Met Val Asn Leu Phe Val
                805                 810                 815

Asn Asp Thr Val Ser Asn Glu Ser Tyr Ile Glu Ser Leu Leu Arg Lys
                820                 825                 830

Glu Pro Glu Ile Asn Ile Glu Glu Lys Glu Pro Gln Ile Ser Ile Glu
            835                 840                 845

Pro Thr His Arg Lys Val Glu Ser Val Ser Cys Met Pro Thr Leu Val
            850                 855                 860

Ala Leu Ser Val Ile Ser Leu Gly Ser Ile Thr Leu Val Thr Gly Met
865                 870                 875                 880

Gly Ile Tyr Ile Cys Leu Arg Lys Gly Glu Lys His Pro Arg Glu Asp
                885                 890                 895
```

```
-continued

Glu Asn Leu Glu Val Gln Ile Pro Leu Lys Gly Lys Ile Asp Leu His
                900                 905                 910

Met Arg Glu Arg Lys Pro Met Asp Ile Ser Asn Ile
        915                 920
```

ANTICANCER AGENT

TECHNICAL FIELD

The present invention relates to a cancer-suppressing gene and medical uses of a protein encoded by the gene.

BACKGROUND ART

It has been known that onset of cancer is induced by mutation or quantitative change of a cell protein. Along with recent development in genetic engineering, it has become possible to amplify a gene encoding a specific protein and to analyze gene mutation in cancer cells, resulting in breakthroughs in the field of cancer research. Hitherto, analysis and identification of oncogenes involved in the canceration of cells and the abnormal growth of cancer cells have made progress. Meanwhile, in recent years, cancer-suppressing genes have been gaining attention. Mutation or the decreased expression level of cancer-suppressing gene leads to canceration of cells. Examples of cancer-suppressing genes that have been identified include Rb gene of retinoblastoma, p 53 gene and APC gene of large-bowel cancer, and WT1 gene of Wilms tumor. For instance, an example of a cancer-suppressing agent that uses WT1 gene has been reported (WO2003/002142).

In addition, it has been gradually revealed that cancer development, malignant progression, and metastasis are caused by abnormalities of not only a single gene but also a plurality of genes. In addition, a greater number of unidentified oncogenes and cancer-suppressing genes are now believed to exist. There are many genes known to have effects that suppress cancer. In most cases, screening for such genes has been carried out by an approach of visually detecting mutation of a patient's gene via staining of chromosomal DNA (Yasuhide Yamashita, et al., World J Gastroenterol, 11 (33): 5129-5135, 2005) or by a method wherein a region of gene deletion is roughly selected based on LOH (loss of heterozygosity) analysis so that important gene regions are narrowed down (WO01/032859). However, such methods are not sufficient as means of discovering cancer-suppressing genes. This is because a tremendous number of DNA deletion regions are detected, so that narrowing them down into important gene regions is extremely time- and labor-consuming, which has been a drawback. Further, conventional separation and discrimination methods for pathological conditions of cancer have only been able to determine malignancy with difficulty.

DISCLOSURE OF THE INVENTION

It is an object of the present invention to provide a cancer-suppressing agent comprising a novel cancer-suppressing gene based on the discovery of such cancer-suppressing gene. Another object of the present invention is to provide a cancer-suppressing agent comprising a protein encoded by the cancer-suppressing gene. Further another object of the present invention is to provide a method for diagnosing the malignancy of the pathological conditions of a cancer patient through measurement of the expression level of the cancer-suppressing gene and methylation of genomic DNA.

To achieve the above objects, the present inventors have intensively searched for partially deleted DNA regions in nonsmall cell lung cancer cases and identified genes differing in methylation degree. Nonsmall cell lung cancer is further classified by tissue type, including adenocarcinoma, carcinoma planoepiteliale, large cell carcinoma, adenosquamous carcinoma, and the like, and it accounts for 80% or more of lung cancer cases. In cancer cells, a genomic region (CpG island) dense with CpG sites existing in the 5' region of a gene (cancer-suppressing gene) suppressing carcinogenesis is abnormally methylated and expression of the messenger RNA may be suppressed, although the major part of such region is normally unmethylated. Such abnormal methylation has recently been recognized as an important carcinogenic mechanism, in addition to gene mutation. In the case of the present invention, in order to specify methylated DNA in nonsmall cell lung cancer, genes deleted at high frequencies in cancer were screened for via a newly developed array CGH method (Inazawa J., et al., Cancer Sci. 95 (7), 559, 2004). Further, the present inventors have succeeded in identifying a gene exhibiting a high degree of DNA methylation and significantly suppressed expression thereof in nonsmall cell lung cancer through the use of a combination of COBRA (combined bisulfite restriction analysis) (Toyota M., et al., Cancer Res. 59, 2307, 1999) and RT-PCR methods. This has led to the completion of the present invention.

Thus, the present invention provides a cancer-suppressing agent which comprises PCDH20 gene (Protocadherin 20: PCDH20, Protocadherin 13) or a homologous gene thereof.

Preferably, the gene or a homologous gene thereof is incorporated into a vector.

Preferably, the vector is a viral vector or plasmid vector for expression in animal cell.

Preferably, the viral vector is a retroviral vector, adenoviral vector, adeno-associated viral vector, baculovirus vector, vaccinia vector, or lentiviral vector.

Preferably, the gene or a homologous gene thereof is encapsulated in a liposome.

Another embodiment of the present invention provides a cancer-suppressing agent which comprises PCDH20 protein or a homologous protein thereof.

Further another embodiment of the present invention provides a method for diagnosing cancer, which comprises a step of analyzing PCDH20 gene in a test sample using DNA or RNA containing PCDH20 gene in its entirety or a part thereof.

Preferably, the analysis involves detection of mutation of the gene or detection of abnormal expression level of the gene.

Preferably, the above diagnostic method of the present invention comprises a step of analyzing methylation of PCDH20 gene in a test sample using DNA containing PCDH20 gene in its entirety or a part thereof.

Further another embodiment of the present invention provides a method for diagnosing cancer, which comprises a step of analyzing PCDH20 protein in a test sample using an antibody against PCDH20 protein or fragment thereof.

Preferably, the analysis involves detection of abnormal expression level of the protein.

BRIEF DESCRIPTION OF THE DRAWINGS

FIG. 7A also shows the results of analyzing 16 cancer tissue samples using MSP primers shown in FIG. 5A (U: unmethylated, M: methylated, N: normal site, and T: tumor site).

BEST MODE FOR CARRYING OUT THE INVENTION

Figure 1:
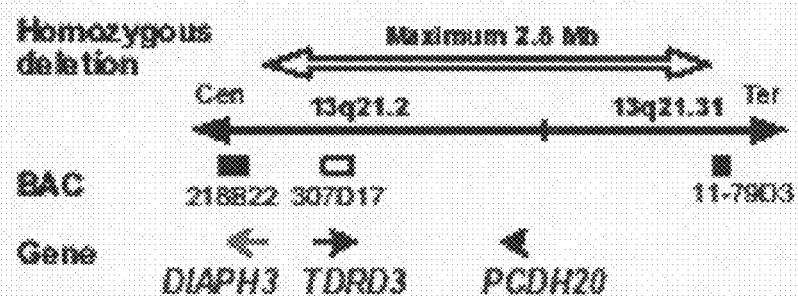
FIG. 1 shows the gene structures of the 21.2 to 21.31 regions of chromosome 13, which are deleted in the VMRC-LCD nonsmall cell lung cancer cell line as obtained by the array CGH method, RP-11 BAC clone existing in the gene regions, and gene.

Hereafter, the embodiments and implementation of the present invention will be described in detail.

(1) Cancer-Suppressing Agent

In accordance with one embodiment of the present invention, the cancer-suppressing agent of the present invention comprises as an active ingredient PCDH20 (Protocadherin 20: PCDH20, Protocadherin 13) gene or a homologous gene thereof. In accordance with another embodiment of the present invention, the cancer-suppressing agent of the present invention comprises as an active ingredient PCDH20 protein or a homologous protein thereof.

The nucleotide sequence of PCDH20 gene and the amino acid sequence of PCDH20 protein have already been known (Kools, P. F. J., Van Roy, F., 1999). The nucleotide sequence of PCDH20 gene has been registered with the database of the National Center for Biotechnology Information (accession no. AF16963). Also, the amino acid sequence of PCDH20 protein has been registered with the same database (accession no. NP073754). The nucleotide sequence of PCDH20 gene is set forth in SEQ ID NO: 1. PCDH20 protein is encoded by the region between positions 72 and 2846 of the nucleotide sequence set forth in SEQ ID NO: 1. The amino acid sequence thereof is set forth in SEQ ID NO: 2.

Herein, the term "PCDH20 gene" refers to a human-derived gene that is specified with the above nucleotide sequence. The term "PCDH20 protein" refers to a protein that is specified with the above amino acid sequence and encoded by PCDH20 gene.

PCDH20 gene may be cDNA obtained from cultured cells using a technique known by persons skilled in the art, or may be synthesized by PCR or the like based on the nucleotide sequence set forth in SEQ ID NO: 1. When DNA having the nucleotide sequence set forth in SEQ ID NO: 1 is obtained by PCR, PCR is carried out using a human chromosomal DNA or a cDNA library as a template and a pair of primers designed to be able to amplify the nucleotide sequence set forth in SEQ ID NO: 1. DNA fragments amplified by PCR can be cloned into an adequate vector that can be amplified in a host such as *Escherichia coli*.

The aforementioned operations, such as probe or primer preparation, cDNA library construction, screening of a cDNA library, and cloning of a target gene, are known to persons skilled in the art. Such operations can be carried out in accordance with methods described in Molecular Cloning: A laboratory Manual, $2^{nd}$ Ed., Cold Spring Harbor Laboratory, Cold Spring Harbor, N.Y., 1989, Current Protocols in Molecular Biology, Supplement 1-38, John Wiley & Sons (1987-1997) and the like.

In accordance with the present invention, the term "homologous gene of PCDH20 gene" refers to: a gene having a nucleotide sequence encoding a protein having cancer-suppressing activity, such nucleotide sequence being derived from the nucleotide sequence set forth in SEQ ID NO: 1 by deletion, addition, or substitution of one or several nucleotides; or a gene having a nucleotide sequence encoding a protein having cancer-suppressing activity, such nucleotide sequence being hybridized with the nucleotide sequence set forth in SEQ ID NO: 1 under stringent conditions. In addition, a fragment of PCDH20 gene is included in the definition of homologous gene of PCDH20 gene.

Regarding the above "nucleotide sequence derived from the nucleotide sequence set forth in SEQ ID NO: 1 by deletion, addition, or substitution of one or several nucleotides," the range of "one to several amino acids" is not particularly limited. For instance, such description indicates 1 to 60 nucleotides, preferably 1 to 30 nucleotides, more preferably 1 to 20 nucleotides, further preferably 1 to 10 nucleotides, and particularly preferably 1 to 5 nucleotides.

The level of "cancer-suppressing activity" above is not particularly limited. However, preferably, such level of cancer-suppressing activity is substantially equivalent to or higher than cancer-suppressing activity of PCDH20 protein (hereafter, the term "cancer-suppressing activity" herein has the meaning given above).

Thus, as long as the "homologous gene of PCDH20 gene" has the structure and function described above, its origin is not particularly limited. Therefore, it may be derived from mammals excluding humans, or may be obtained by artificially introducing mutation into a gene derived from mammals such as humans. Note that when the gene is used as a cancer-suppressing agent as described below, it is preferable that the gene be derived from humans in view of clinical safety.

The aforementioned "gene having a nucleotide sequence encoding a protein having cancer-suppressing activity, such nucleotide sequence being derived from the nucleotide sequence set forth in SEQ ID NO: 1 by deletion, addition, or substitution of one or several nucleotides" can be produced by any methods known by persons skilled in the art such as chemical synthesis, gene engineering techniques, and mutagenesis methods. Specifically, the aforementioned gene can be obtained by utilizing DNA having the nucleotide sequence set forth in SEQ ID NO: 1 and introducing mutation into the DNA. For instance, a method wherein DNA having the nucleotide sequence set forth in SEQ ID NO: 1 is allowed to come into contact with an agent serving as a mutagen, a method of UV irradiation, a gene engineering technique, and the like can be used. Site-directed mutagenesis is one of gene engineering techniques. It is useful because a specific mutation can be introduced into a specific site. This technique can be carried out in accordance with, for example, Molecular Cloning, A laboratory Manual, $2^{nd}$ Ed., Cold Spring Harbor Laboratory, Cold Spring Harbor, N.Y., 1989; Current Protocols in Molecular Biology, Supplements 1-38, John Wiley & Sons (1987-1997).

The aforementioned "nucleotide sequence being hybridized under stringent conditions" refers to a nucleotide sequence of DNA obtained by colony hybridization, plaque hybridization, Southern hybridization, or the like using DNA as a probe. For instance, an example of the DNA used is DNA that can be identified by carrying out hybridization at 65° C. in the presence of 0.7 to 1.0 M NaCl using a filter in which DNA derived from a colony or plaque or a fragment thereof is immobilized, followed by washing of the filter at 65° C. using 0.1 to 2×SSC solution (1×SSC solution comprises 150 mM sodium chloride and 15 mM sodium citrate). Hybridization can be carried out in accordance with methods described in Molecular Cloning: A laboratory Manual, $2^{nd}$ Ed., Cold Spring Harbor Laboratory, Cold Spring Harbor, N.Y., 1989.

An example of DNA hybridized under stringent conditions is DNA having a certain level or more of homology to the nucleotide sequence of DNA used as a probe. For instance, such DNA has a homology of 70% or more, preferably 80% or more, more preferably 90% or more, further preferably 93% or more, and particularly preferably 95% or more to the DNA used as a probe.

The aforementioned "gene having a nucleotide sequence encoding a protein having cancer-suppressing activity, such nucleotide sequence being hybridized with the nucleotide sequence set forth in SEQ ID NO: 1 under stringent conditions" can be obtained as described above by colony hybridization, plaque hybridization, or Southern hybridization under certain hybridization conditions.

In accordance with the present invention, "homologous protein of PCDH20 protein" refers to: a protein having an amino acid sequence derived from the amino acid sequence set forth in SEQ ID NO: 2 by deletion, substitution, and/or insertion of one to several amino acids, the amino acid sequence having cancer-suppressing activity; or a protein having an amino acid sequence which is 70% or more homologous to the amino acid sequence set forth in SEQ ID NO: 2, the amino acid having cancer-suppressing activity.

Regarding the above "nucleotide sequence derived from the nucleotide sequence set forth in SEQ ID NO: 2 by deletion, substitution, or insertion of one or several amino acids," the range of "one to several amino acids" is not particularly limited. For instance, such description indicates 1 to 20 amino acids, preferably 1 to 10 amino acids, more preferably 1 to 7 amino acids, further preferably 1 to 5 amino acids, and particularly preferably 1 to 3 amino acids.

The above "amino acid sequence which is 70% or more homologous to the amino acid sequence set forth in SEQ ID NO: 2" indicates that such amino acid is at least 70% or more, preferably 80% or more, and more preferably 90% or more homologous to the amino acid sequence set forth in SEQ ID NO: 2.

PCDH20 protein may be a naturally occurring protein, a chemically synthesized protein, or a recombinant protein produced by gene recombination technology. In view of large scale production through relatively easy operations, a recombinant protein is preferable.

A naturally occurring protein can be isolated from a cell or tissue in which the protein has been expressed by an adequate combination of protein isolation methods. A chemically synthesized protein may be synthesized by chemical synthesis methods such as the Fmoc method (fluorenylmethyloxycarbonyl method) and the tBoc method (t-butyloxycarbonyl method). In addition, the protein of the present invention can be synthesized using a variety of commercially available peptide synthesis machines. A recombinant protein can be produced by introducing DNA having a nucleotide sequence encoding the protein (e.g., the nucleotide sequence set forth in SEQ ID NO: 1) into a suitable expression system.

In addition, a protein having an amino acid sequence derived from the amino acid sequence set forth in SEQ ID NO: 2 by deletion, substitution, or insertion of one to several amino acids or a protein having an amino acid sequence which is 70% or more homologous to the amino acid sequence set forth in SEQ ID NO: 2 can be adequately produced or obtained by persons skilled in the art based on the nucleotide sequence set forth in SEQ ID NO: 1, which is one example of the sequences of DNA encoding the amino acid sequence set forth in SEQ ID NO: 2.

A preferred embodiment of the cancer-suppressing agent of the present invention comprises, as an active ingredient, a recombinant vector which is obtained by incorporating the above PCDH20 gene or a homologous gene thereof into such vector. An example of the vector used is a virus vector or a vector for expression in animal cell. Preferably, a virus vector is used.

Examples of such viral vector include a retroviral vector, an adenoviral vector, an adeno-associated viral vector, a baculovirus vector, a vaccinia vector, and lentiviral vector. Among them, a retroviral vector is particularly preferably used. This is because, after a viral vector infects with a cell, a virus genome is incorporated into a host chromosome such that a gene incorporated into the vector can be stably expressed for a long period of time.

As an example of a vector for expression in animal cell, pCXN2 (Gene, 108, 193-200, 1991), PAGE207 (JP Patent Publication (Kokai) No. 6-46841 (1994)), or a modified vector thereof may be used.

The above recombinant vector can be produced by introducing it into an adequate host for transformation and culturing the obtained transformant. When the recombinant vector is a viral vector, an animal cell capable of producing virus is used as a host into which the vector is introduced. Examples of such animal cell include COS-7 cell, CHO cell, BALB/3T3 cell, and HeLa cell. Examples of a host used for a retroviral vector include ψCRE, ψCRIP, and MLV. An example of a host used for an adenoviral vector and an adeno-associated viral vector is 293 cell derived from a human embryonic kidney. A viral vector can be introduced into an animal cell by a calcium phosphate method or the like. In addition, when a recombinant vector is a vector for expression in animal cell, as a host into which the vector is introduced, *Escherichia coli* K12, HB101, DH5 α, or the like can be used. Transformation of *Escherichia coli* has been known to persons skilled in the art.

The obtained transformants are each cultured in an adequate medium under adequate conditions. For instance, a transformant of *Escherichia coli* can be cultured using a liquid medium (for example, pH 5 to 8) containing carbon sources, nitrogen sources, inorganic matter and the like, which are necessary for cell growth. In general, culture is carried out at 15° C. to 43° C. for about 8 to 24 hours. In such case, a recombinant vector of interest can be obtained after the termination of culture by general DNA isolation methods.

Further, transformants of animal cells can be cultured using media such as 199 medium, MEM medium, and DMEM medium containing about 5% to 20% of bovine fetal serum. The pH of the medium is preferably about 6 to 8. In general, culture is carried out at about 30° C. to 40° C. for about 18 to 60 hours. In such case, since viral particles containing a recombinant vector are dispersed into a culture supernatant, a recombinant vector of interest can be obtained as a result of concentration and purification of viral particles by cesium chloride centrifugation, polyethylene glycol precipitation, and filter concentration.

As an example of the cancer-suppressing agent of the present invention, a cancer-suppressing agent (hereafter referred to as gene therapeutic agent) comprising as an active ingredient PCDH20 gene or a homologous gene thereof, can be produced by mixing PCDH20 gene or a homologous gene thereof as an active ingredient with a base generally used for a gene therapeutic agent. In addition, when PCDH20 gene or a homologous gene thereof is incorporated into a viral vector, viral particles containing a recombinant vector are prepared and the particles are mixed with a base generally used for a gene therapeutic agent.

As the above base, a base generally used for an injection can be used. Examples thereof include distilled water, a salt solution containing sodium chloride or a mixture of sodium chloride and an inorganic salt, a solution containing mannitol, lactose, dextran, glucose or the like, an amino acid solution of glycine, arginine or the like, and a mixed solution of an organic acid or salt solution and a glucose solution. Alternatively, in accordance with conventional techniques known by persons skilled in the art, using an adjuvant such as an osmoregulator, a pH adjuster, a plant oil, or a surfactant with such base, an injection can be prepared as a solution, suspension, or dispersion. Such injection can be prepared as a pharmaceutical that is solubilized at the time of use through operations such as pulverization and freeze drying.

In addition, the gene therapeutic agent of the present invention can be produced by adding PCDH20 gene to a liposome suspension prepared in accordance with conventional techniques, followed by freezing and thawing. Liposomes can be prepared by filter penetration, ultrasonication, reverse phase evaporation, surfactant removal, or the like. Preferably, a gene is added to a liposome suspension that has been subjected to ultrasonication for reasons of the improved efficiency of gene encapsulation. A liposome encapsulating a gene can be intravenously administered alone or while suspended in water, saline, or the like.

The above gene therapeutic agent can be administered by general systematic administration through veins, arteries and the like, or local administration such as local injection or oral administration to a primary lesion of cancer or a predictable metastatic site. Further, administration of the gene therapeutic agent can also take place by a combination of catheterization, gene introduction, or surgical operations.

The dosage of the above gene therapeutic agent varies depending on patient's age, sex, and symptoms, the route of administration, the number of doses, and dosage forms. In general, the daily dosage (the weight of recombinant gene) ranges from 1 μg/kg body weight to 1000 mg/kg body weight for adults. Preferably, it ranges from 10 μg/kg body weight to 100 mg/kg body weight. The number of doses is not particularly limited.

Further, as an example of the cancer-suppressing agent of the present invention, a cancer-suppressing agent (hereafter referred to as protein formulation) comprising as an active ingredient PCDH20 protein or a homologous protein thereof is provided in the form of pharmaceutical composition comprising as an active ingredient PCDH20 protein or a homologous protein thereof and a pharmaceutical additive (e.g., a carrier or an excipient).

The form of the above protein formulation is not particularly limited. Examples of such form for oral administration include tablets, capsules, fine granules, powders, granules, liquids, and syrups. Examples of such form for parenteral administration include injections, infusions, suppositories, inhalants, transmucosa absorption systems, and transdermal absorption systems.

The route of administration of the above protein formulation is not particularly limited. The formulation can be administered by either oral administration or parenteral administration (e.g., intramuscular administration, intravenous administration, intradermal administration, transmucosa administration such as peritoneal administration, and inhalation administration).

The daily dosage of the above protein therapeutic agent varies depending on the patient's age, sex, symptoms, the route of administration, the number of doses, and the dosage form. In general, the daily dosage ranges from 0.001 μg/kg body weight to 1000 μg/kg body weight for adults. Preferably, it ranges from 0.001 μg/kg body weight to 100 μg/kg body weight. The number of doses is not particularly limited.

The above cancer-suppressing agent (including both forms of a gene therapeutic agent and a protein formulation) can be used for suppressing cancer by administering the effective dose thereof to mammalian animals including humans. The above cancer-suppressing agent can be used to prevent and/or treat cancer by administering the effective dose thereof for prevention and/or therapy to mammalian animals including humans.

The term "cancer-suppressing" herein has a broad meaning to a maximum extent, including preventive effects of preventing development, metastasis and implantation of cancer and therapeutic effects of inhibiting cancer cell growth, halting progression of cancer by reducing the size of cancer, and improving symptoms. In any case, it should not be interpreted in a limited manner.

Examples of cancer to be treated with the cancer-suppressing agent of the present invention include, but are not limited to, malignant melanoma, malignant lymphoma, lung cancer, esophageal cancer, gastric cancer, large-bowel cancer, rectal cancer, colon cancer, urinary tract tumor, gallbladder cancer, bile duct cancer, biliary tract, breast cancer, liver cancer, pancreatic cancer, testis tumor, maxillary cancer, tongue cancer, lip cancer, oral cavity cancer, pharynx cancer, larynx cancer, ovarian cancer, uterine cancer, prostate cancer, thyroid gland cancer, brain tumor, Kaposi's sarcoma, angioma, leukemia, polycythemia vera, neuroblastoma, retinoblastoma, myeloma, bladder tumor, sarcoma, osteosarcoma, myosarcoma, skin cancer, basal-cell carcinoma, cutaneous appendage tumor, skin metastatic cancer, and skin melanoma. In addition, among these, nonsmall cell lung cancer is particularly preferable as a target of treatment.

(2) Diagnostic Method for Cancer Using the PCDH20 Gene

Examples of the diagnostic method for cancer of the present invention include a method for diagnosing the malignancy of cancer and a diagnostic method for selecting cancer cases to which the anticancer agent of the present invention may be applied. The method for diagnosing cancer of the present invention comprises the step of analyzing PCDH20 gene in a test sample using DNA or RNA containing PCDH20 gene in its entirety or a part thereof.

Herein, a part of PCDH20 gene is, for example, an oligonucleotide having a nucleotide sequence comprising about 10 to 30 consecutive nucleotides constituting the nucleotide sequence of the PCDH20 gene set forth in SEQ ID NO: 1. Examples of a test sample that can be used include tissue section, blood, lympha, sputum, lung lavage liquid, urine, feces, and tissue culture supernatant, which are suspected to contain the presence of tumor.

The above expression "detection to screen for cancer to which the cancer-suppressing agent of the present invention is applied" indicates discovering the presence or absence of cancer in tissue or the like, on which the cancer-suppressing agent of the present invention effectively acts.

Diagnosis of cancer is carried out by analyzing PCDH20 gene in a test sample using DNA or RNA containing PCDH20 gene in its entirety or a part thereof as a primer or probe. Specifically, the expression "analyzing PCDH20 gene" used herein indicates detection of methylated genomic DNA or detection of an abnormal level of gene expression.

Detection of gene mutation is carried out as follows. When the above DNA or RNA is used as a primer, a partial sequence of DNA prepared from a test sample is amplified by PCR using, for example, selected two types of primers having different sequences, followed by treatment with sodium hydrogen sulfite. Thus, unmethylated cytosine (C) in the genomic DNA is converted into uracil (U). Since methylated cytosine is structurally stable, it does not undergo such reactions and is not converted into uracil. The presence of methylated DNA can be confirmed by analyzing unmethylated cytosine and cytosine that has been modified as a result of being combined with a restriction enzyme susceptive to the influence of methylation, after being subjected to restriction enzyme cleavage (COBRA). Alternatively, such detection can be carried out by: amplifying a partial sequence of DNA prepared from a test sample by PCR; allowing the amplified product to be subjected to treatment with sodium hydrogen sulfite; incorporating the amplified product into a plasmid; transforming a host cell with it and culturing the transformant; and analyzing the nucleotide sequence of the clone obtained.

Meanwhile, detection of abnormal levels of gene expression can be carried out by Northern hybridization or RT-PCR (reverse transcription-polymerase chain reaction) using a probe containing the above RNA sequence.

(3) Method for Diagnosing Cancer Using PCDH20 Protein Antibody or a Fragment Thereof.

The method for diagnosing cancer of the present invention comprises a step of analyzing the amount of PCDH20 proteins in a test sample using an antibody against PCDH20 protein or a fragment thereof.

The antibody against the PCDH20 protein used in the present invention (hereafter referred to as PCDH20 antibody) can be produced by a conventional method using PCDH20 protein in its entirety or a part thereof as an antigen. The term "a part of an PCDH20 protein" indicates a polypeptide comprising at least 6 amino acids, preferably about 8 to 10 amino acids, and further preferably about 11 to 20 amino acids, which are consecutive amino acids constituting the amino acid sequence of the PCDH20 protein set forth in SEQ ID NO: 2. The PCDH20 protein in its entirety or a part thereof serving as an antigen may be prepared by either biological or chemical techniques.

A polyclonal antibody can be prepared in the following manner: the above antigen, for example, is repeatedly used for subcutaneous, intramuscular, intraperitoneal, and intravenous inoculation in animals such as mice, guinea pigs, and rabbits such that the animals are sufficiently immunized; blood is collected from the animals; and serum separation is performed. A monoclonal antibody can be prepared from a culture supernatant of a hybridoma or ascites of a mouse into which the hybridoma has been administered, such hybridoma being obtained by cell fusion of commercially available mouse myeloma cells and splenic cells of a mouse immunized with, for example, the above antigen.

It is possible to measure the expression level of PCDH20 protein in a test sample using PCDH20 protein antibody or a fragment thereof prepared as described above. For instance, the measurement of the expression level can be carried out using Western blotting or immunological methods such as immunoblotting, enzymeimmunoassay (EIA), radioimmunoassay (RIA), a fluorescent antibody method, and immunocyto-staining. Herein, a fragment of PCDH20 protein antibody refers to a single-chain fragment variable (scFv) of an antibody of interest or the like. In addition, examples of a test sample that can be used include tissue section, blood, lympha, sputum, alveolar lavage liquid, urine, feces, and tissue culture supernatant, which are suspected to exhibit the presence of tumor. The low expression level of PCDH20 protein in a test sample subjected to measurement indicates that the expression of the PCDH20 gene is suppressed in the sample tissue or cells. Therefore, cancer to which the cancer-suppressing agent of the present invention is applied can be screened for.

The present invention is hereafter described in greater detail with reference to the following examples, but the technical scope of the present invention is not limited thereto.

EXAMPLES (1) Experimental Materials

Cell lines used herein were squamous cell lines EBC-1, LK-2, PC10, VMRC-LCP, LC-1sq, and ACC-LC-73; adenocarcinoma cell lines 11-18, A549, ABC-1, RERF-LC-OK, VMRC-LCD, SK-LC-3, and RERF-LC-KJ; and large cell carcinoma cell lines KNS-62, 86-2, LU65, PC-13, ACC-LC-33, NCI-H460, and LU99A. As lung cancer samples derived from clinical specimens, paraffin-embedded samples derived from 53 types of adenocarcinoma and rapidly-frozen samples derived from 59 types of adjacent normal site were used. Cancer samples derived from clinical specimens were obtained from the National Cancer Center, Hokushin General Hospital of Nagano Prefectural Welfare Federation and used under agreement with each patient and approval of the ethical committee of each organization. Moreover, clinical specimen donors were not subjected to radiation, chemical therapy, or immunological therapy before sampling. In addition, in order to obtain a material with inhibited DNA methylation, 5-aza-deoxycytidine (5-aza-dCyd) serving as a DNA methyltransferase inhibitor was added to each cell type at a concentration of 5 mM for 5 days during culture. In order to observe histone deacetylation effects, trichostatin A (TSA) serving as a non-specific inhibitory substance for histone deacetylase was added at a concentration of 100 ng/ml for 12 hours during culture before cell harvest.

(2) Separation of Deleted DNA from Nonsmall Cell Lung Cancer Cells by Array CGH Method Nonsmall cell lung cancer cell lines were screened for a homozygously deleted gene via the array CGH method using an MCG Whole Genome Array-4500 (Inazawa J., et al., Cancer Sci. 95(7), 559, 2004). DNA derived from a cancer cell was labeled with Cy3 and then mixed with a healthy subject control sample labeled with Cy5, followed by hybridization. BAC clones (each exhibiting a logarithmic value of −2.0 or lower (with 2 as the lowest) obtained by dividing the fluorescent signal intensity of the former DNA by the same of the latter DNA) and the genes contained in such clones are listed in Table 1. Deleted regions were found in various lung cancer cells; that is, gene deletion represented by cancer-suppressing gene CDKN2 was detected. The present inventors focused on a PCDH20 gene that had never been discussed in terms of its relationship with cancer. The PCDH20 gene is a gene located in the vicinity of BAC clone No. RP11-307D17 and is present in chromosome 13 q21.2. The deletion of this region was confirmed in the VMRC-LCD cell line.

TABLE 1

BAC clones separated as deleted DNAs from nonsmall cell lung cancer cells by the array CGH method, positions in the vicinity of the BAC clones, and genes contained in the BAC clones

| No. | BAC | Locus[a] | | Cell line (Total 20) | | Possible candidate gene[b] | Number of known genes |
|---|---|---|---|---|---|---|---|
| | | Chr. Band | Position | n | Name | | |
| 1 | RP11-178M15 | 1p36.21 | chr1:13,731,635-13,731,966 | 1 | 11-18 | PRDM2 | 2 |
| 2 | RP11-79M24 | 6p25 | chr6:1,754,013-1,926,781 | 1 | KNS-62 | GMDS | 1 |
| 3 | RP11-31F19 | 9p24.3 | chr9:537,217-682,143 | 1 | LC-1 sq | ANKRD15 | 7 |
| | RP11-143M15 | 9p24.3 | chr9:812,146-991,152 | 1 | LC-1 sq | | |
| 4 | RP11-113D19 | 9p21.3 | chr9:20,996,400-21,158,464 | 1 | VMRC-LCD | CDKN2A, CDKN2B, MTAP | 22 |
| | RP11-344A7 | 9p21.3 | chr9:21,506,373-21,676,227 | 4 | VMRC-LCD, LC-1 sq, KNS-62 | | |
| | RP11-11J 1 | 9p21.3 | chr9:22,417,726-22,579,721 | 1 | KNS-62 | | |
| | RP11-782K2 | 9p21.3 | chr9:22,584,981-22,585,358 | 1 | KNS-62 | | |
| 5 | RP11-33O15 | 9p21.3 | chr9:22,823,087-22,897,484 | 2 | KNS-62, LU99A | TEK | 6 |
| | RP11-330J23 | 9p21.3 | chr9:25,292,197-25,425,886 | 2 | KNS-62, LU99A | | |
| | RP11-55P9 | 9p21.3-21.2 | chr9:25,425,787-25,573,596 | 1 | LU99A | | |
| 6 | RP11-307D17 | 13q21.2 | chr13:58,727,654-61,368,564 | 1 | VMRC-LCD | PCDH20 | 2 |

TABLE 1-continued

BAC clones separated as deleted DNAs from nonsmall cell lung cancer cells by the array CGH method, positions in the vicinity of the BAC clones, and genes contained in the BAC clones

| No. | BAC | Locus[a] Chr. Band | Position | n | Cell line (Total 20) Name | Possible candidate gene[b] | Number of known genes |
|---|---|---|---|---|---|---|---|
| 7 | RP11-600P1 | 13q31.1 | chr13:77,973,420-78,566,321 | 1 | VMRC-LCP | | 4 |
| | RP11-25J23 | 13q31.1 | chr13:78,837,347-79,310,431 | 1 | VMRC-LCP | | |
| | RP11-440G4 | 13q31.1 | chr13:81,026,555-81,027,175 | 1 | VMRC-LCP | | |
| | RP11-295L12 | 13q31.1 | chr13:81,571,893-82,147,460 | 1 | VMRC-LCP | | |
| | RP11-400M8 | 13q31.1 | chr13:82,201,212-82,280,653 | 1 | VMRC-LCP | | |
| | RP11-91O15 | 13q31.1 | chr13:83,668,529-83,670,196 | 1 | VMRC-LCP | | |
| | RP11-118K20 | 13q31.1 | chr13:83,711,618-83,853,235 | 1 | VMRC-LCP | | |
| | RP11-29C8 | 13q31.1 | chr13:84,853,779-85,313,978 | 1 | VMRC-LCP | | |
| | RP11-569I20 | 13q31.1 | chr13:85,891,468-86,093,892 | 1 | VMRC-LCP | | |
| | RP11-29P20 | 13q31.2 | chr13:86,796,651-87,270,500 | 1 | VMRC-LCP | | |
| | RP11-27D9 | 13q31.2 | chr13:87,913,237-88,370,388 | 1 | VMRC-LCP | | |
| | RP11-114G1 | 13q31.3 | chr13:88,656,527-89,117,305 | 1 | VMRC-LCP | | |
| | RP11-86C3 | 13q31.3 | chr13:88,883,889-89,379,578 | 1 | VMRC-LCP | | |
| | RP11-79H7 | 13q31.3 | chr13:89,556,363-90,080,636 | 1 | VMRC-LCP | | |
| 8 | RP11-72J7 | 13q32.2 | chr13:97,465,157-97,495,769 | 1 | VMRC-LCD | EBI2 | 10 |
| | RP11-19J14 | 13q32.2 | chr13:97,851,595-97,851,757 | 1 | VMRC-LCD | | |
| | RP11-122A8 | 13q32.3 | chr13:98,471,182-98,644,517 | 1 | VMRC-LCD | | |
| 9 | RP11-134G22 | 20p12.1 | chr20:15,224,211-15,251,444 | 2 | SK-LC-3, KNS-62 | | 0 |
| | RP11-65G18 | 20p12.1 | chr20:15,271,770-15,375,903 | 1 | SK-LC-3 | | |
| | RP11-11O15 | 20p12.1 | chr20:15,567,963-15,728,758 | 1 | SK-LC-3 | | |

[a]Based on UCSC Genome Browser, May 2004 Assembly.
[b]Possible tumor suppressor genes located around BAC.

(3) Structure in the Vicinity of BAC Clone No. RP11-307D17 Containing the PCDH20 Gene FIG. 1 shows the structure containing the PCDH20 gene (confirmed to be deleted in VMRC-LCD cell line) in the vicinity of chromosome 13 q21.2. A 2.5-mega-base (Mb) portion contains a deleted region (Homozygous Deletion) indicated by a white arrow. A genomic DNA structure in the vicinity of the PCDH20 gene within the 2.5-mega-base portion contains two genes (TDRD3 and PCDH20).

(4) Presence of the TDRD3 and PCDH20 Genes in the Genomes of Various Cells

Figure 2:
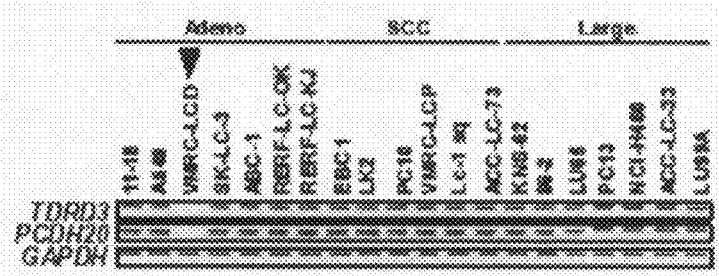
FIG. 2 shows the results of extracting DNAs from adenocarcinoma cell lines (Adeno)11-18, A549, VMRC-LCD, SK-LC-3, ABC-1, RERF-LC-OK, and RERF-LC-KJ; squamous cell lines (SCC) EBC-1, LK-2, PC10, VMRC-LCP, LC-1 sq, and ACC-LC-73; large cell carcinoma cell lines (Large) KNS-62, 86-2, LU65, PC-13, NCI-H460, and ACC-LC-33; and LU99A cell lines; carrying out PCR using specific primers of the TDRD3 and PCDH20 gene regions; and then detecting the presence of each gene in the genomes by electrophoresis. The lower column shows the result of detection using GAPDH as a positive control.

DNA was extracted from adenocarcinoma cell lines (Adeno) 11-18, A549, VMRC-LCD, SK-LC-3, ABC-1, RERF-LC-OK, and RERF-LC-KJ; squamous cell lines (SCC)EBC-1, LK-2, PC10, VMRC-LCP, LC-1 sq, and ACC-LC-73; and large cell carcinoma cell lines (Large) KNS-62, 86-2, LU65, PC-13, NCI-H460, ACC-LC-33, and LU99A. The presence of the genomes of TDRD3 (Tudor domain containing protein 3) and PCDH20 gene regions in the extracted DNAs was detected via PCR. FIG. 2 shows the results. Deletion of the TDRD3 and PCDH20 genes was detected in the VMRC-LCD cell line. However, in the other cell lines, deletion at the genomic DNA level was not confirmed. A GAPDH (glyceraldehyde-3 phosphate-dehydrogenase) gene was used as a positive control.

(5) Expression of Messenger RNA of PCDH20 Gene

Figure 3:
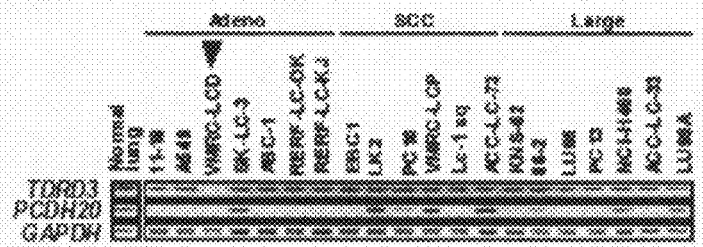
FIG. 3 shows electrophoresis images obtained by carrying out RT-PCR of the TDRD3 and PCDH20 genes. Specifically, RT-PCR was carried out for 20 nonsmall cell lung cancer cell lines (11-18, A549, VMRC-LCD, SK-LC3, ABC-1, RERF-LC-OK, RERF-LC-KJ, EBC-1, LK2, PC10, VMRC-LCP, LC-1 sq, ACC-LC-73, KNS-62, 86-2, LU65, PC-13, NC1—H460, ACC-LC-33, and LU99A) and a normal lung sample as a control in order to measure the expression of messenger RNA of PCDH20 gene. GAPDH was used as a control for the expression levels determined by RT-PCR.

Twenty nonsmall cell lung cancer cell lines were subjected to RT-PCR (FIG. 3) using a normal lung sample as a control for measuring the expression level of messenger RNA of PCDH20 gene. The expression level of GAPDH was used as a control in RT-PCR because the expression level of GAPDH is known to not easily change depending on cell species and conditions. No expression of messenger RNA of TDRD3 gene and no expression of messenger RNA of PCDH20 gene were observed in the VMRC-LCD cell line having DNA deficient in the TDRD3 and PCDH20 genes, as was expected. Furthermore, whereas DNA was present in many cell lines, some cell species (11-18, A549, VMRC-LCD, ABC-1, RERF-LC-OK, RERF-LC-KJ, EBC-1, PC10, LC-1 sq, KNS-62, 86-2, LU65, PC-13, and ACC-LC-33) exhibited low-level or no expression of messenger RNA of PCDH20 gene. This phenomenon implies the involvement not of mutation at the genomic level but of epigenetic mechanisms in gene expression.

Figure 4:
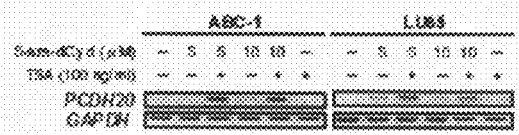
FIG. 4 shows the results of comparing 2 cell lines (ABC-1 and LU65) in terms of the expression levels of messenger RNA of PCDH20 gene. Specifically, the results were obtained by adding either 5-aza-deoxycytidine (5-aza-dCyd) serving as a DNA methyltransferase inhibitor to each cell type at concentrations of 5 or 10 μM for 5 days and/or trichostatin A (TSA) serving as a non-specific inhibitory substance for histone deacetylase to each cell type at concentrations of 100 ng/ml or 100 ng/ml for 12 hours before cell harvest during culture, and then carrying out RT-PCR, followed by comparison of the expression levels of PCDH20 gene messenger RNA via electrophoresis. The expression level of GAPDH was used as a control in RT-PCR.

(6) Comparison Between the Expression Levels of Messenger RNAs of Methylated and Demethylated PCDH20 Gene Under general culture conditions, messenger RNA of PCDH20 gene was expressed using 2 cell lines (ABC-1 and LU65). The 2 cell lines were cultured by adding 5-aza-deoxycytidine (5-aza-dCyd) serving as a DNA methyltransferase inhibitor at concentrations of 5 μM and 10 μM for 5 days or trichostatin A (TSA) serving as a non-specific inhibitory substance for histone deacetylase at a concentration of 100 ng/ml for 12 hours before cell harvest, or both thereof. Subsequently, the expression levels of messenger RNA of PCDH20 gene were compared via RT-PCR (FIG. 4). The expression level of GAPDH was used as a control in RT-PCR. It was confirmed for both cell lines tested that the transcription suppression was canceled by the DNA methylation inhibitor and the transcription levels were elevated synergistically with histone deacetylation.

(7) Promoter Structure and Methylation of the PCDH20 Gene

Figure 5:
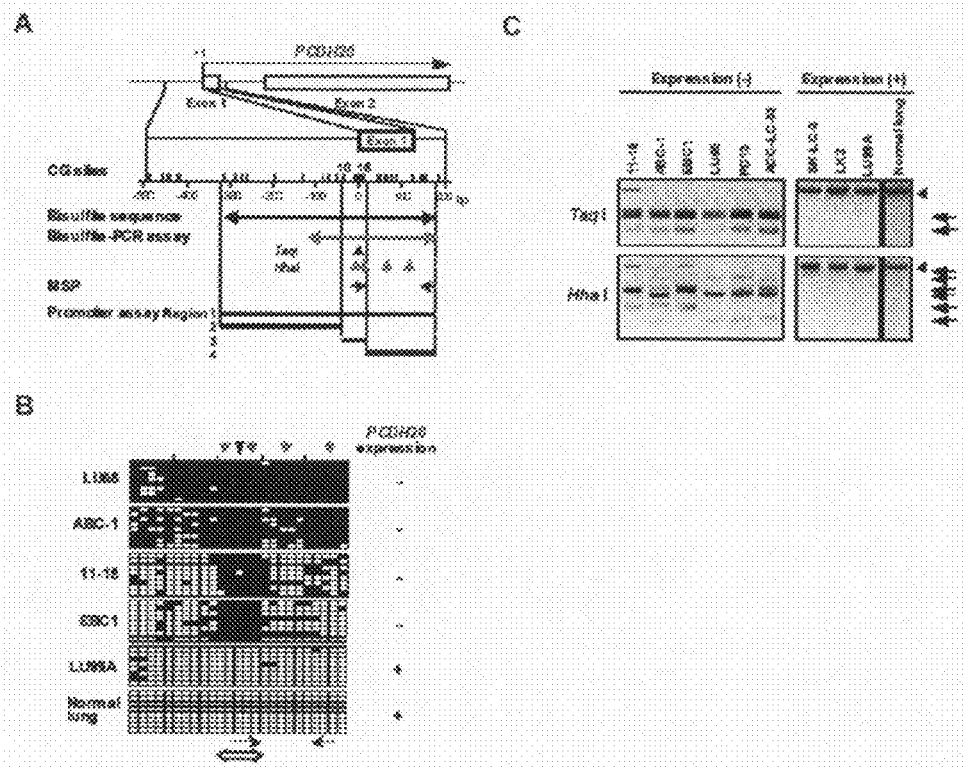
FIG. 5A shows the DNA structure in the vicinity of exon 1 of the PCDH20 gene. "CG sites" are sites where CpG sequences are present in this gene region. A "bisulfite sequence" is a region (specifically, a 494-nucleotide range (region between –314 and +180) within the DNA region in the vicinity of exon 1 of the PCDH20 gene of a cancer cell) for which methylation in the CpG sites; that is, changes in the nucleotide sequence were analyzed after treatment with sodium hydrogen sulfite. A region indicated with the term "bisulfite-PCR assay" is a region for which methylation in the CpG sites was analyzed via cleavage with restriction enzymes Taq I and Hha I capable of recognizing conversion of cytosine (C) to uracil (U) following treatment with sodium hydrogen sulfite. A site indicated with the term "Bisulfite-PCR assay" is a site cleaved by each of these restriction enzymes. A position indicated with the term "MSP" is a forward primer position or a reverse primer position, by which nucleotide mutation that takes place before or after treatment with sodium hydrogen sulfite at positions ranging from CpG10 to CpG15 can be precisely recognized. "Promoter assay regions" are 4 types of gene region, which were used for reporter assay carried out for regions in the vicinity of the transcription initiation point of the PCDH20 gene.
FIG. 5B shows the results of analyzing methylation (via nucleotide sequence analysis following treatment with sodium hydrogen sulfite) in the 25 CpG sites existing within the DNA region in the vicinity of exon 1 of the PCDH20 gene. Specifically, DNA derived from LU65, ABC-1, 11-18, and EBC-1 which were observed not to express the PCDH20 gene, LU99A expressing the PCDH20 gene, and a normal lung tissue were subjected to the analysis. Methylated regions are indicated with a black color.
FIG. 5C shows the electrophoresis images obtained by analyzing 11-18, ABC-1, EBC-1, LU65, PC-13, and ACC-LC-33 cell lines expressing the PCDH20 gene at low levels (Expression (−)), SK-LC-3, LK-2, and LU99A observed to express the PCDH20 gene (Expression (+)), and a normal lung sample by the COBRA method using cleavage patterns resulting from the use of restriction enzymes Taq I and Hha I. Fragment positions generated by C-to-U conversion in CpG followed by cleavage with the restriction enzymes are indicated with arrows. Fragment positions with no cleavage points are indicated with wedge marks.

A DNA sequence in the vicinity of exon 1 of the PCDH20 gene lacked a typical CpG island structure, but contained 25 CpG sites over 446 nucleotides (between −290 nucleotide and +156 nucleotide; +1 was the transcription initiation point), indicating the presence of relatively many CpGs (FIG. 5A). Gene mutation is detected by preparing a partial DNA sequence from a test sample, amplifying the partial DNA sequence via the PCR method using 2 selected types of primer sequence, and then treating the resultant with sodium hydrogen sulfite. Thus, unmethylated cytosine (C) in the genomic DNA is converted into uracil (U). Since methylated cytosine is structurally stable, it does not undergo the above-mentioned reactions and is not converted into uracil. Alternatively, methylation can be detected by: amplifying via the PCR method a partial DNA sequence prepared from a test sample; treating the amplified product with sodium hydrogen sulfite; incorporating the amplified product into a plasmid; transforming host cells with the plasmid; culturing the host cells; and then analyzing the nucleotide sequence of the thus obtained clone (Bisulfite-sequence method). Methylation in a 494-nucleotide range (region between −314 to +180) in the vicinity of exon 1 of the PCDH20 gene was analyzed (FIG. 5B) by the method. LU65, ABC-1, 11-18, and EBC-1 observed not to express the PCDH20 gene and LU99A expressing the PCDH20 gene were subjected to methylation analyses. Among the CpG sites existing at 25 positions, methylated sites were denoted with a black color and compared with normal-lung-tissue-derived DNA. It was revealed that the methylation degree of the promoter region is inversely correlated with PCDH20 gene expression and that the hypermethylated sites among the 25 CpG sites contained a region from roughly CpG10 to CpG15.

A method for detecting gene mutation is as follows. Unmethylated cytosine (C) in genomic DNA is converted to uracil (U) using the presence or the absence of treatment with sodium hydrogen sulfite. Since methylated cytosine is structurally stable, it does not undergo such reactions and is not converted into uracil. PCR detection is carried out using such resultant as a template, and then amplified DNA products derived from altered cytosine and the same derived from unmethylated cytosine are analyzed via restriction enzyme cleavage using a combination of restriction enzymes to be affected by methylation. Hence, the presence of methylated DNA can be specified (COBRA method: an experimental method using a Bisulfite-PCR method and a restriction enzyme cleavage method in combination). Accordingly, methylation in the vicinity of exon 1 of the PCDH20 gene was detected by the COBRA method (FIG. 5C). In the cases of 11-18, ABC-1, EBC-1, LU65, PC-13, and ACC-LC-33 cell lines expressing the PCDH20 gene at low levels, 2 cleaved DNAs and 6 cleaved DNAs were observed because of the presence of Taq I and Hha I (restriction enzymes) cleavage sites as a result of electrophoresis (arrow). Meanwhile, in the cases of SK-LC-3, LK-2, and LU99A and the normal lung sample observed to express the PCDH20 gene, digestion with both restriction enzymes did not result in the generation of restriction enzyme cleavage sites in a manner depending on methylation. Therefore, single bands were observed as a result of electrophoresis (wedge mark).

Figure 6:
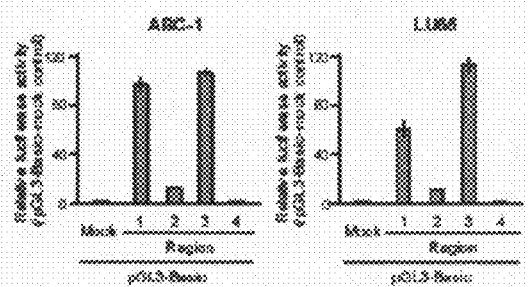
FIG. 6 shows the results of reporter assays for determining the presence or the absence of transcription-promoting activity in ABC-1 or LU65 cells using luciferase enzyme activity. Specifically, the reporter assays were carried out after the transfer of a 494-nucleotide region (region between –314 and +180) in the vicinity of exon 1 of the PCDH20 gene or a fragment (FIG. 5A) thereof into the ABC-1 or LU65 cells observed not to express the PCDH20 gene.

(8) The Transcription-Promoting Effect of the PCDH20 Gene Promoter Region as Determined by the Reporter Assay The presence or the absence of transcription-promoting activity in a 494-nucleotide range (region between −314 and +180) in the vicinity of exon 1 of the PCDH20 gene and a fragment thereof (FIG. 5A) was verified via reporter assay. The reporter assay system employed herein was based on a method for measuring a light-emitting substance resulting from the expression of the messenger RNA of a firefly luciferase enzyme, conversion of the mRNA into a protein, and then the functioning of the protein as an active enzyme. The luciferase gene was disposed downstream of a pGL3-Basic vector (Promega). Constructs containing PCDH20 gene regions 1 to 4 as promoter analysis regions were introduced into ABC-1 and LU65 cells observed not to express the PCDH20 gene and then the enzyme activity was determined (FIG. 6). The entire 494-nucleotide region and region 3 exhibited high luciferase enzyme activity for both cell types. It was thus revealed that a basic unit of the transcription activation region of the PCDH20 gene is located in region 3.

Figure 7:
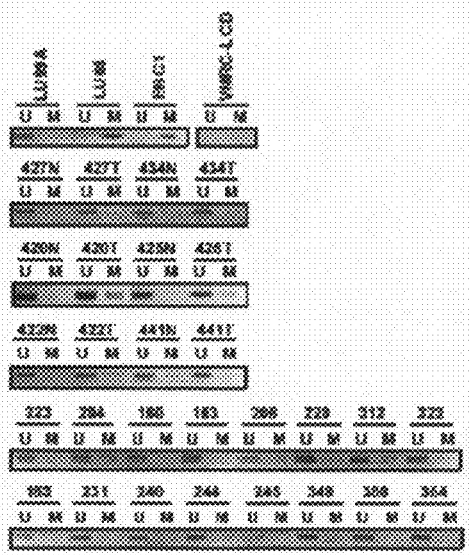
FIG. 7A shows the results of analyzing the following 6 samples via the MSP method: lung cancer cell lines LU99A, LU65, EBC1, and VMRC-LCD; a clinically derived normal tissue sample; and a clinically derived cancer tissue sample (both were analyzable).
FIG. 7B shows the results of analyzing methylation in 420 and 425, regarding which differences in methylation were detected, and 434, regarding which no differences in methylation were detected, by the Bisulfite-sequence method. Methylated sites are indicated with a black color.
FIG. 7C shows the results of detecting PCDH20 gene messenger RNA in 420, 425, and 434 via RT-PCR. The lower column indicates the expression level of GAPDH used as a control.
Figure 7:
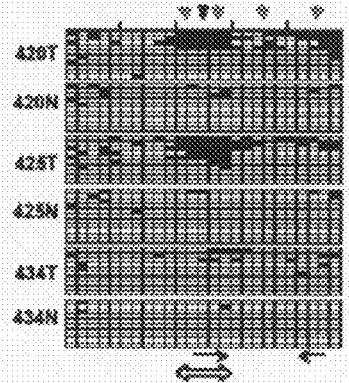
Figure 7:
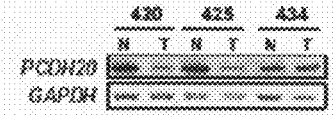

A method for detecting methylation in promoter regions is as described below. Unmethylated cytosine (C) in genomic DNA can be converted to uracil (U) through treatment with sodium hydrogen sulfite. After treatment with sodium hydrogen sulfite, PCR is carried out for the subject DNA using a primer pair corresponding to uracil at the altered site. Thus, methylation at specific sites can be detected (Methylation Specific PCR method: MSP). With the use of this method, lung cancer cell lines LU99A, LU65, and EBC1, the VMRC-LCD cell line lacking the PCDH20 gene in the DNA, clinically derived adjacent normal tissue samples, and cancer tissue samples were analyzed using MSP primers as shown in FIG. 5A (FIG. 7A; U: unmethylated, M: methylated, N: normal site, and T: tumor site). In the cases of lung cancer cell lines, promoter sites were methylated in both EBC1 and LU65 cell lines not expressing the PCDH20 gene as determined by the MSP method. In the case of LU99A cells expressing the PCDH20 gene, the promoter sites were not methylated as expected. Methylation in 32 out of 59 clinical non-small cell cancer samples could be analyzed via the MSP method. Among 7 out of 12 samples for which analyses of the cancer tissues and adjacent normal sites had been possible, methylation was detected at cancer sites but not detected at the adjacent normal sites in the cases of 4 out of 7 samples (FIG. 7A: electrophoresis column Nos. 3-4). Samples regarding which differences in methylation had been detected and samples (420, 425, and 434) regarding which no differences in the same had been detected were subjected to the following methylation analyses. Specifically, these samples were subjected to methylation analyses via the bisulfite-sequence method in the 494-nucleotide range (region between −314 and +180) in the vicinity of exon 1 of the PCDH20 gene (FIG. 7B). In cancer cases 420 and 425 regarding which differences in methylation had been detected, methylation was observed in a region between CpG10 and CpG15 as expected but methylation was detected at very low levels in the adjacent normal sites (methylated sites are indicated with a black color). Meanwhile, in the case of 434 regarding which no methylation had been observed by the MSP method, hypermethylation was not observed in either cancer or adjacent normal sites. Furthermore, PCDH20 gene messenger RNA in the same samples was detected by RT-PCR (FIG. 7C). It was confirmed that compared with cancer case 434, regarding which differences in methylation had not been detected, PCDH20 gene messenger RNA had been expressed at lower levels in the cancer cases 420 and 425 as expected, regarding which differences in methylation had been detected.

(9) Decrease in Carcinogenicity Due to PCDH20 Gene Transfer into Lung Cancer Cells Adherence to solid matter is known as an example of the differences in properties between normal cells and cancer cells under culture conditions. Specifically, it is necessary for normal cells to adhere to solid matter for cell proliferation (anchorage dependence). When normal cells are cultured in a soft agar medium (about 0.33%), they cannot proliferate while floating in such medium. However, many cancer cells lack anchorage dependence so that they can proliferate in a soft agar medium. Since floating cancer cells cannot move in a soft agar medium, a single cancer cell is repeatedly divided such that the divided cells form colonies within 1 to 3 weeks. Since there is a correlation between such cells' ability to form soft agar colonies and ability to form a tumor via implantation, the degree of such ability has been widely used as an indicator of malignancy (Shin, S. I., et al., Proc. Natl. Acad.

Figure 8:
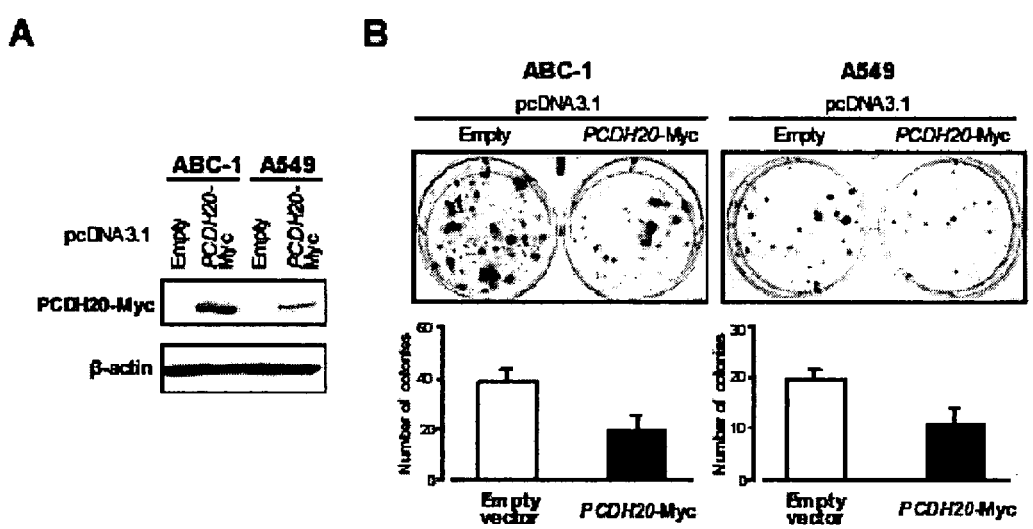
FIG. 8A shows the results of observation of the expression of an myc protein and the expression of a β-actin protein as a positive control via the Western-blot method using 10 μg of a cell lysis solution at 48 hours after the transfer of pCMV3.1 or pCMV3.1-PCDH20-Myc into ABC-1 or A549 cells.
FIG. 8B shows the results of determination of the number of colonies obtained by 3 weeks of culture of the 4 above types in combination in soft agar media, followed by crystal violet staining.

Sci. U.S.A. 72, 4435, 1975). A full-length PCDH20 cDNA was inserted into a pCMV3.1 vector (Stratagene) in which an myc peptide can be added to the amino C-terminus of an inserted gene (pCMV3.1-PCDH20-Myc). The gene was transferred to ABC-1 and A549 cells observed not to express the PCDH20 gene using FuGENE6 (Roche Diagnostics). The cells were cultured in a soft agar medium for 3 weeks in the presence of 500 mg/ml G418 (Geneticin). After crystal violet staining, the number of colonies was counted (FIG. 8B). At the same time, an experiment that involves gene transfer using negative control "Empty" (pCMV3.1) was also carried out. The cells into which the 4 above gene types had been transferred were observed. Specifically, myc protein expression and β-actin protein (positive control) expression in 10 μg each of cell lysis solutions were observed by the Western-blot method at 48 hours after gene transfer. The presence of a pPCDH20-Myc fusion protein was confirmed in only cell species into which pCMV3.1-PCDH20-Myc had been transferred, as expected (FIG. 8A). In both cases of ABC-1 and A549 cells, it was confirmed that the number of colonies was significantly reduced due to PCDH20 gene expression, unlike the results in the cases of Empty. This phenomenon indicates that the PCDH20 gene has a function of suppressing cancer cell proliferation. Thus, the gene has been revealed to function as a cancer-suppressing gene in lung cancer cells.

Figure 9:
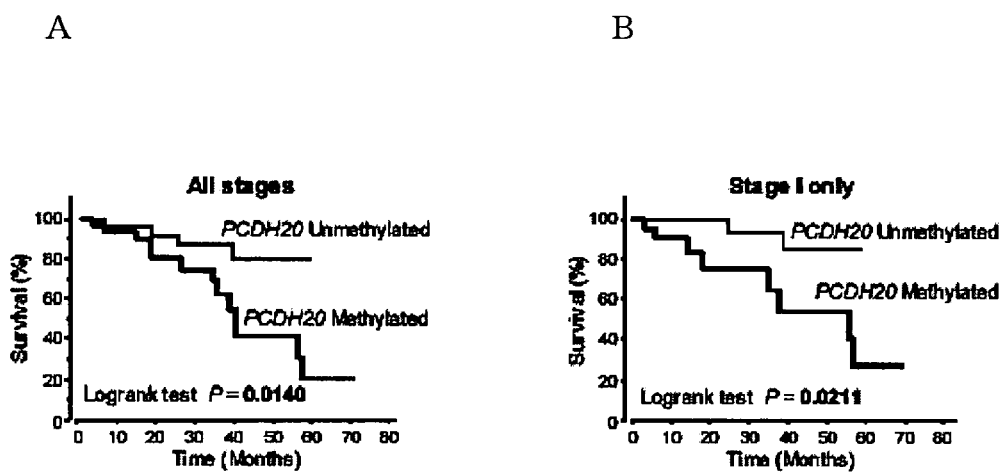
FIG. 9A shows the survival information upon and after sampling according to the Kaplan-Meier method. Specifically, the survival information was obtained after MSP analyses had been conducted on 59 clinical samples derived from nonsmall cell lung cancer patients. Survival rates are plotted on the longitudinal axis and survival periods are plotted on the horizontal axis. A thin line indicates a patient for which no methylation was detected in the PCDH20 gene promoter region and a thick line indicates a patient for which methylation was detected in the PCDH20 gene promoter region.
FIG. 9B shows the analytical results obtained in a manner similar to that of FIG. 9A, concerning the survival information of 39 samples of stage I patients alone.

(10) Relationship Between Methylation in the PCDH20 Gene Promoter Region and Survival of Lung Cancer Patients For 59 clinical samples derived from nonsmall cell lung cancer patients, survival information upon and after sampling was analyzed based on MSP analyses and using the Kaplan-Meier method. Survival rates are plotted on the longitudinal axis and survival periods are plotted on the horizontal axis. A thin line indicates a patient for which no methylation was detected in the PCDH20 gene promoter region and a thick line indicates a patient for which methylation was detected in the PCDH20 gene promoter region (FIG. 9A). P value was found to be 0.0140 in the Logrank test, confirming significant correlation between the two. Similar analyses were made on the survival information of stage I patients alone using the samples derived from such patients. As a result, P value was found to be 0.0211, confirming significant correlation between methylation and survival period even in such early cancer cases (FIG. 9B). This fact means that malignancy (life expectancy) of nonsmall cell lung cancer patients can be predicted through measurement of methylation in the PCDH20 gene promoter region or the expression levels of the messenger RNA.

(11) Conclusion (a) The PCDH20 gene having a hypermethylated site in its genomic DNA and exhibiting lower messenger RNA expression levels in nonsmall cell lung cancer was isolated by screening with the use of the array CGH method. It was also demonstrated by experiments using cells derived from clinical samples that lowered PCDH20 gene expression levels are restored by the cancellation of methylation in the genomic DNA.

(b) It was revealed that a region (in the vicinity of exon 1) in the genomic DNA of the PCDH20 gene possesses ability to cause transcriptional activation and the methylation thereof contributes to lower messenger RNA expression levels. It was also revealed by analyses of clinical samples that methylation in such region correlates with malignancy (life expectancy) that cannot be predicted with stage progression alone of nonsmall cell lung cancer. It was further revealed that high PCDH20 gene expression levels inversely correlate with methylation in such region.

(c) After the PCDH20 gene was transferred into a nonsmall cell lung cancer cell line not expressing the PCDH20 gene, the degree of cell proliferation decreased in an experiment of anchorage dependence. Thus, it was revealed that the expression of the PCDH20 gene as a protein causes cancer cells to lose their own properties; that is, the PCDH20 gene functions as a cancer-suppressing gene.

EFFECTS OF THE INVENTION

In accordance with the present invention, there is provided a cancer-suppressing agent which comprised PCDH20 gene, which has been newly found to have a function of suppressing cancer, or PCDH20 protein encoded by this gene. These agents are very useful in view of clinical applications such as the treatment based on individual differences of cancers and the improvement of cancer prognosis, or in view of basic cancer research. Furthermore, malignancy (life expectancy) of a nonsmall cell lung cancer patient can be predicted by measuring methylation in a PCDH20 gene promoter region or the expression level of the messenger RNA thereof.

The invention claimed is:

1. A method for diagnosing nonsmall cell lung cancer, which comprises a step of analyzing PCDH20 gene in a lung sample using DNA or RNA containing PCDH20 gene in its entirety or a part thereof, wherein deletion of PCDH20 gene in genome or decreased expression level of PCDH20 gene is detected to diagnose nonsmall cell lung cancer.

* * * * *